US010120976B2

(12) United States Patent
Natarajan et al.

(10) Patent No.: US 10,120,976 B2
(45) Date of Patent: Nov. 6, 2018

(54) METHODS, SYSTEMS, AND COMPUTER READABLE MEDIA FOR INTEGRATING MEDICAL IMAGING DATA IN A DATA WAREHOUSE

(71) Applicant: Oracle International Corporation, Redwood Shores, CA (US)

(72) Inventors: Prashant Natarajan, Livermore, CA (US); Brian A. Pederson, San Francisco, CA (US)

(73) Assignee: Oracle International Corporation, Redwood Shores, CA (US)

( * ) Notice: Subject to any disclaimer, the term of this patent is extended or adjusted under 35 U.S.C. 154(b) by 417 days.

(21) Appl. No.: 14/682,066

(22) Filed: Apr. 8, 2015

(65) Prior Publication Data

US 2016/0300015 A1    Oct. 13, 2016

(51) Int. Cl.
*G06F 17/30* (2006.01)
*G06F 19/00* (2018.01)

(52) U.S. Cl.
CPC ...... *G06F 19/321* (2013.01); *G06F 17/30563* (2013.01); *G06F 17/30592* (2013.01)

(58) Field of Classification Search
CPC .................. G06F 17/30563; G06F 17/30592
See application file for complete search history.

(56) References Cited

U.S. PATENT DOCUMENTS

| | | | | |
|---|---|---|---|---|
| 2003/0120458 A1* | 6/2003 | Rao | ....................... | G06F 17/3061 |
| | | | | 702/181 |
| 2011/0153351 A1* | 6/2011 | Vesper | ................... | G06Q 10/10 |
| | | | | 705/2 |
| 2015/0339359 A1* | 11/2015 | Takaoka | ............ | G06F 17/30292 |
| | | | | 707/602 |
| 2016/0147946 A1* | 5/2016 | Von Reden | ........... | G06F 19/322 |
| | | | | 705/3 |

OTHER PUBLICATIONS

Kagadis et al.; "Anniversary Paper: Roles of medical physicists and health care applications of informatics," Medical Physics, vol. 35, No. 1, pp. 119-127 (Jan. 2008), http://www.iornp.org/sites/default/files/anniversary_paper_kagadis.pdf.
"Oracle Multimedia: DICOM Developer's Guide," 11g Release 1 (11.1) (May 2009).

(Continued)

*Primary Examiner* — Khanh B Pham
(74) *Attorney, Agent, or Firm* — Jenkins, Wilson, Taylor & Hunt, P.A.

(57) ABSTRACT

Methods, systems, and computer readable media for integrating medical imaging data in a data warehouse are disclosed. According to one method, the method occurs at a data warehouse management server that manages a data warehouse system. The data warehouse management server includes at least one processor. The method includes receiving medical imaging data including imaging metadata from an imaging related data source. The method also includes storing the imaging metadata in the data warehouse. The method further includes performing data processing using the imaging metadata and other healthcare related data stored in the data warehouse, wherein the other healthcare related data is from one or more different data sources.

20 Claims, 5 Drawing Sheets

(56) References Cited

OTHER PUBLICATIONS

"Computed Tomography (CT) Accreditation Program: Clinical Data Form," American College of Radiology (Sep. 14, 2010).
"A Very Basic DICOM Introduction," dcm4che.org (Mar. 24, 2011), file:///l:/Tekelec/1322-518/refs%20to%20cite/A%20Very%20Basic%20DICOM%20Introduction%20-%20dcm4che-2.x%20-%20Confluence.html.
Stewart, "Introduction to Medical Imaging—Chapter 1; Radiatian and the Atom—Chapter 2," Lecture (Jan. 31, 2013), http://courses.washington.edu/radxphys/course_content/r2/imaging_radn_and_atom/class_2012/Intro_Radiation_Atom-2013-01-31a-4pp.pdf.
McEnery, "Radiology Information Systems and Electronic Medical Records: IT Reference Guide for the Practicing Radiologist," American College of Radiology (2013), http://www.acr.org/~/media/ACR/Documents/PDF/Advocacy/IT Reference Guide/IT Ref Guide RISEMR.
DICOM PS 3.6 2013—Data Dictionary (2013), http://medical.nema.org/dicom/2013/output/pdf/part06.pdf.
DICOM PS 3.3 2013—Information Object Definitions, p. 71-76 (2013), http://medical.nema.org/dicom/2013/output/pdf/part03.pdf.
"Oracle Healthcare Data Warehouse Foundation: Secure Installation and Configuration Guide," Release 6.0 (Jun. 2014).
"American College of Radiology CT Accreditation Program: Testing Instructions," (Jul. 24, 2015), http://www.acr.org/~/media/ACR/Documents/Accreditation/CT/ClinicalTestingInstructions.pdf.
"The DICOM Standard 2015," Digital Imaging and Communications in Medicine, Medical Imaging & Technology Alliance, NEMA (2015), http://medical.nema.org/standard.html.
Accreditation—American College of Radiology, http://www.acr.org/Quality-Safety/Accreditation/ (Retrieved Jan. 14, 2016).

\* cited by examiner

| DICOM TAGS | CONVERSION RULES | STORAGE LOCATIONS |
|---|---|---|
| R | RULE 1 | IMAGE STUDY - ATTRIBUTE A, IMAGE SERIES - ATTRIBUTE C, IMAGE INSTANCE - ATTRIBUTE E |
| S | RULE 2, RULE 3 | IMAGING DEVICE - ATTRIBUTE D |
| T | RULE 4 | IMAGING DEVICE -- ATTRIBUTE B |
| U | RULE 1, RULE 3 | IMAGE STUDY - ATTRIBUTE F |
| V | RULE 5 | IMAGE INSTANCE - ATTRIBUTE G, OBSERVATION - ATTRIBUTE H |

METHODS, SYSTEMS, AND COMPUTER READABLE MEDIA FOR INTEGRATING MEDICAL IMAGING DATA IN A DATA WAREHOUSE

TECHNICAL FIELD

The subject matter described herein relates to a data warehouse. More particularly, the subject matter described herein relates to systems, methods, and computer readable media for integrating medical imaging data in a data warehouse.

BACKGROUND

Medical imaging is the creation of visual representation of medical relevant data, which can be captured by a number of procedures, modalities, and/or technologies, e.g., light projection, electromagnetic projection, ultrasonic wave projection, thermography, elastography, magnetic resonance, nuclear medicine functional techniques, mammography, electrocardiography (EKG), computed tomography (CT), X-ray CT, positron emission tomography, and others. Medical imaging and/or related procedures may generate medical imaging data and may include metadata describing the procedure used to acquire the image(s), metadata describing the acquired image(s), and/or other information about the visual representation (e.g., image) or a related imaging device.

Accordingly, there exists a need for systems, methods, and computer readable media for integrating medical imaging data in a data warehouse.

SUMMARY

Methods, systems, and computer readable media for integrating medical imaging data in a data warehouse are disclosed. According to one method, the method occurs at a data warehouse management server that manages a data warehouse system. The data warehouse management server includes at least one processor. The method includes receiving medical imaging data including imaging metadata from an imaging related data source. The method also includes storing the imaging metadata in the data warehouse. The method further includes performing data processing using the imaging metadata and other healthcare related data stored in the data warehouse, wherein the other healthcare related data is from one or more different data sources.

According to one system, the system includes at least one processor and a data warehouse management server that manages a data warehouse. The data warehouse management server includes the at least one processor. The data warehouse management server is configured to receive medical imaging data including imaging metadata from an imaging related data source, to store the imaging metadata in the data warehouse, and to perform data processing using the imaging metadata and other healthcare related data stored in the data warehouse, wherein the other healthcare related data is from one or more different data sources.

The subject matter described herein may be implemented in hardware, software, firmware, or any combination thereof. As such, the terms "function", "node" or "module" as used herein refer to hardware, software and/or firmware components for implementing the feature(s) being described. In one implementation, the subject matter described herein may be implemented using a non-transitory computer readable medium having stored thereon computer executable instructions that when executed by the processor of a computer cause the computer to perform steps. computer readable media suitable for implementing the subject matter described herein include non-transitory computer-readable media, such as disk memory devices, chip memory devices, programmable logic devices, random access memory (RAM), read only memory (ROM), optical read/write memory, cache memory, magnetic read/write memory, flash memory, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which.

DETAILED DESCRIPTION

The subject matter described herein relates to methods, systems, and computer readable media for integrating medical imaging data in a data warehouse. Medical imaging is involved in multiple disciplines, and is far more than diagnostic radiology. Interventional radiology, radiation therapy, gated imaging studies, and many other procedures have emerged and are gaining popularity in diagnosis and treatment of various diseases. Many medical imaging procedures generate an image or visual representation along with relevant metadata describing the procedure used to acquire the image(s) and other relevant information. For example, such metadata may reveal information about the quality, accuracy, appropriateness, and safety of an imaging procedure and/or other aspects. Moreover, imaging metadata may be usable for optimizing patient safety, spatial and temporal resolution, and costs associated with these imaging procedures.

Prior to the subject matter described herein, data warehouse systems did not integrate medical imaging data and/or related metadata with data from other healthcare related enterprise systems (e.g., an electronic heath record (EHR) system, an enterprise resource planning (ERP) system, a healthcare related scheduling system, or a healthcare related financial system). Moreover, data warehouse systems did not provide a data warehouse model providing imaging integration and did not provide functionality to analyze the integrated data, e.g., by combining high-quality and versioned imaging metadata with other healthcare related information about the patient, device, intervention, observation, encounter, accounting and financial data, claims, and billing information for enabling analysis of the different aspects of the healthcare service provided to one or more patients.

In accordance with some aspects of the subject matter described herein, methods, mechanisms, and/or techniques for integrating medical imaging data in a data warehouse. For example, a data warehouse management system or a related entity in accordance with one or more aspects of the present subject matter can integrate imaging metadata with other data sources, ensure the persistence of high quality, mastered data in a data warehouse model, and simultaneously leverage that data for analytics.

Reference will now be made in detail to embodiments of the presently disclosed subject matter, examples of which are illustrated in the accompanying drawings. Wherever possible, the same reference numbers will be used throughout the drawings to refer to the same or like parts. Various embodiments of the present subject matter are disclosed and described herein.

Figure 1:
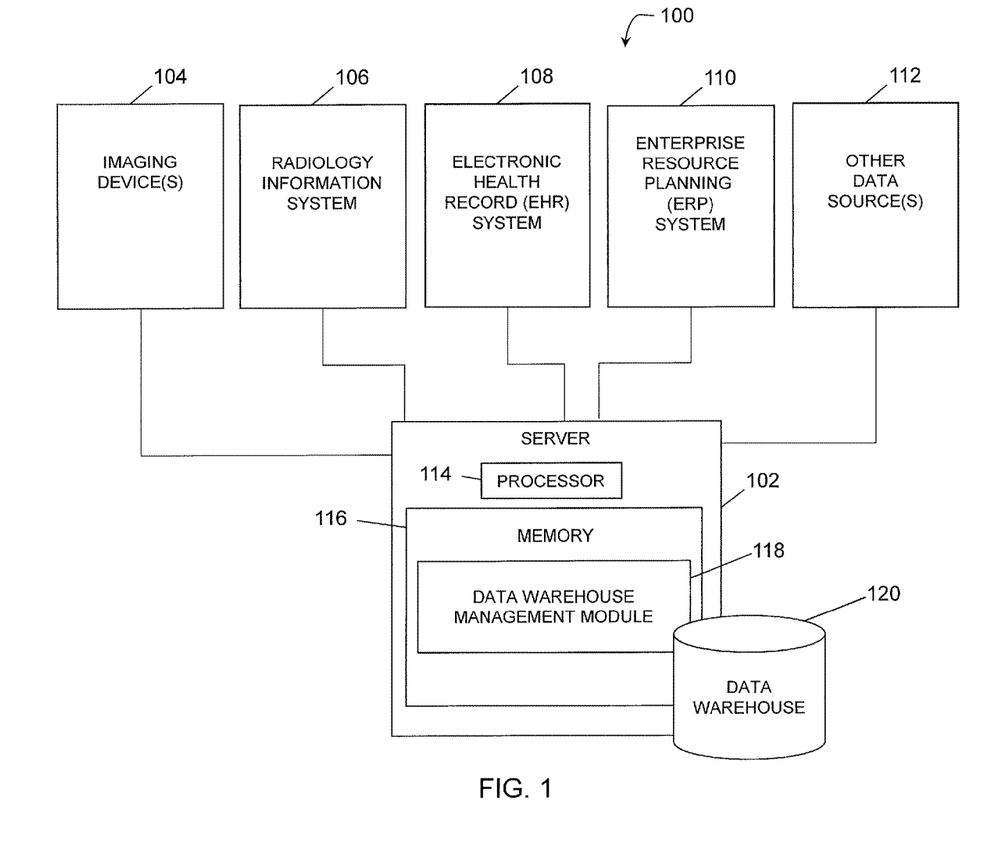
FIG. 1 is a block diagram illustrating a data warehouse system according to an embodiment of the subject matter described herein.

FIG. 1 is a block diagram illustrating a data warehouse system 100 according to an embodiment of the subject matter described herein. Referring to FIG. 1, data warehouse system 100 can include a data warehouse management (DWM) server 102 that is communicatively connected to various data sources, e.g., one or more imaging device(s) 104, a radiology information system (RIS) 106, an electronic health record (EHR) system 108, an enterprise resource planning (ERP) system 110, and other data sources (e.g., a healthcare related enterprise financial system and/or a healthcare related scheduling system).

In some embodiments, each of DWM server 102 and data sources 104-112 may comprise a special purpose computing device or machine that includes hardware components (e.g., one or more processor units, memory, and network interfaces) configured to execute software elements (e.g., applications, software modules, etc.) for the purposes of performing one or more aspects of the disclosed subject matter herein. In addition, it should be noted that DWM server 102 and its components and functionality described herein may constitute a special purpose computer that improves the technological field pertaining to healthcare related data warehouse systems by providing mechanisms for integrating medical imaging data (e.g., imaging metadata) with data from various healthcare related enterprise systems.

Imaging device(s) 104 represent any suitable entity or entities (e.g., a computing platform, software executing on a processor, a logic device, an ASIC, and/or an FPGA) for performing medical imaging procedure, generating images, generating or obtaining imaging metadata, and/or related functions. For example, imaging device(s) 104 may create images using various imaging technologies, e.g., light projection, electromagnetic projection, ultrasonic wave projection, thermography, elastography, mammography, magnetic resonance, nuclear medicine functional techniques, electrocardiography (EKG), computed tomography (CT), X-ray CT, positron emission tomography, and others.

In some embodiments, imaging device(s) 104 may generate metadata or information about one or more images generated. For example, imaging device(s) 104 may provide metadata as native DICOM output and/or may be integrated into a DICOM compatible system. In this example, imaging device(s) 104 may act as a DICOM client, sending its output to a DICOM server (e.g., DWM server 102 or RIS 106), which may receive and store the images and their metadata.

In some embodiments, imaging device(s) 104 may automatically fill out metadata about itself (e.g., tube voltage, table speed, etc.) and/or may receive information that the operator enters (e.g., patient ID, Name, etc.) via a user interface (e.g., a graphical user interface (GUI) and may provide this information to DWM server 102 and/or DWMM 118.

In some embodiments, DWM server 102 and/or DWMM 118 may store medical imaging data (e.g., imaging metadata) and/or gather additional information about the patient or medical imaging data by obtaining data from other data sources 106-112. For example, imaging metadata can be stored in data warehouse 120 and can be integrated with clinical and administrative information about a given patient, device, intervention, observation, encounter, accounting and financial data, and claims and billing information. In this example, the data stored in data warehouse 120 may enable analysis of different aspects of healthcare services provided to one or more patients.

RIS 106 represents any suitable entity or entities (e.g., a computing platform, software executing on a processor, a logic device, an ASIC, and/or an FPGA) for controlling and documenting radiology workflows and services provided to patients, e.g., by radiology departments. For example, RIS 106 may store transactions related to medical imaging, such as orders, reports, and even scheduling and appointments. In this example, RIS 106 may represent a specialized EMR system for imaging. In some embodiments, RIS 106 may act as a broker between EMR system 108 and DWM server 102 or other entities, e.g., by communicating with the various systems using different protocols or mechanisms.

EHR system 108 represents any suitable entity or entities (e.g., a computing platform, software executing on a processor, a logic device, an ASIC, and/or an FPGA) for storing clinical information and/or transactional data about patients. For example, EHR system 108 may store information about patient demographics, encounters, interventions, orders, observations, claims, bills, etc. In another example, EHR system 108 may also include one or more other similar systems (e.g., hospital information system (HIS)) and/or related data. In some embodiments, EHR system 108 may represent a source of patient clinical and administrative data unrelated to medical imaging data.

ERP system 110 represents any suitable entity or entities (e.g., a computing platform, software executing on a processor, a logic device, an ASIC, and/or an FPGA) for storing resource information and planning information. For example, ERP system 110 may store information about medical equipment and/or healthcare personnel. In this example, ERP system 110 may be usable for scheduling personnel, reserving and/or ordering medical equipment, scheduling surgeries, and/or other functions.

Other data source(s) 112 represent any suitable entity or entities (e.g., a computing platform, software executing on a processor, a logic device, an ASIC, and/or an FPGA) for providing medical related data. For example, data source(s) 112 may include picture archiving and communication system (PACS) for storing, retrieval, querying, and transforming medical images. In this example, the PACS system may support a DICOM interface and act as a DICOM server. In another example, a PACS system may also act as a DICOM client and send imaging data to other servers or entities.

As indicated above, data warehouse system 100 may include DWM server 102, which is communicatively connected (e.g., via a local network or the Internet) to each of data sources 104-112. In some embodiments, DWM server 102 may include a processor 114 (which may be operatively coupled to a bus) for processing information and executing instructions or operations. Processor 114 may be any type of processor, such as a central processor unit (CPU), a microprocessor, a multi-core processor, and the like. DWM server 102 may further include a memory 116 for storing information and instructions to be executed by processor 114.

In some embodiments, memory 116 can comprise one or more of random access memory (RAM), read only memory (ROM), static storage such as a magnetic or optical disk, or any other type of machine or non-transitory computer-readable medium. DWM server 102 may further include a communication device (not shown), such as a network interface card or other communications interface, configured to provide communications access to data sources 104-112. In some embodiments, memory 116 may be utilized to store a DWM module (DWMM) 118 and a data warehouse 120.

DWMM 118 may represent any suitable entity or entities (e.g., a computing platform, software executing on a processor, a logic device, an ASIC, and/or an FPGA) for managing data warehouse system 100 and/or data warehouse 120. For example, DWMM 118 may be configured to process and manage data from heterogeneous data sources 104-112. In some embodiments, DWMM 118 may comprise a software algorithm (executable by one or more processors) that is configured to receive and process medical related data, including medical imaging data and imaging metadata, from one of data sources 104-112 and may convert and/or store this information in a data warehouse 120.

In some embodiments, various data sources, such as imaging device(s) 104, RIS 106, and/or a PACS system, may provide DICOM data to DWM server 102 and/or DWMM 118 in one or more formats. For example, one format is a DCM file, e.g., with each image in a single file, containing one or more DICOM tag-value pairs. These tag-value pairs may define the image, for example a tag of (0008, 0022) is followed by the Study Date (e.g., the date the image was captured/generated). Another tag, (7FE0, 0010) Pixel Data, is followed by raw data of an actual image. In DCM files, tags may be presented in a flat, continuous format and there is no distinction of information entities (IEs) or objects. They also contain a single image, and for modalities with multiple images, the metadata is repeated at the top of each image file.

Another DICOM format involves a DICOMDIR file or protocol, which consists of two or more files and is usually used when two DICOM applications are communicating over some physical media, e.g., a DVD or a flash drive. Using this format, there is one DICOMDIR file, which contains records of nodes (e.g., IEs), each having a type like patient, image study, image series, and image instance. Each node may include metadata in the form of key-value attributes, e.g., patient ID and patient name for the patient nodes. As such, the DICOMDIR format distinguishes between objects (e.g., IEs or groups of related modules) and modules (e.g., groups of related attributes). The DICOMDIR file then contains paths to the files on the media that contain only the pixel data. The other file(s) in the DICOMDIR format lack any metadata for indicating which node in the DICOMDIR file they belong. In other words, if the directory structure and file names are lost or altered then there is no way of finding which image data is for which metadata by looking at the contents of the DICOMDIR or pixel-data files.

Another DICOM format includes a DICOM Message, which is used when two DICOM applications are communicating over TCP/IP network. For example, DICOM message may be sent via a state-less TCP/IP connection but may be treated as a stateful DICOM connection. In this example, a sender may send multiple DICOM messages to the receiver under the context of a session, e.g., first transferring metadata about an image series (e.g., a group of images) in one transaction and then pixel data of each image in the image series in subsequent transactions.

In some embodiments, DWMM 118 may include functionality for integrating output of multiple imaging device(s) 104 and/or other DICOM data sources by using vendor-provided data in transforming or converting the data into a compatible format for storing in data warehouse 120. For example, DICOM is a vast and extensive standard. DICOM currently includes more than 3500 tags organized in 139 modules (e.g., groups of tags or attributes) and not all of these tags or modules pertain to every device. For a given device, a vendor may create a document called DICOM Conformance Statement, which shows the subsets of tags that a specific device can provide with the images they take. A DICOM Conformance Statement may also specify vendor specific tags.

Additional details for identifying, converting, storing, and/or using DICOM information can be found in "Oracle® Multimedia DICOM Developer's Guide", 11g Release 1 (11.1), May 2009, http://docs.oracle.com/cd/B28359_01/appdev.111/b28416.pdf; the disclosure of which is incorporated herein by reference in its entirety.

In some embodiments, DWMM 118 may include functionality for converting DICOM related data types into compatible data types for storing in data warehouse 120. For example, DICOM data may be received by DWMM 118 as a character string formatted in special way that is called value representations (VR) in DICOM. DICOM currently has about 28 different VR types, most of them easily convertible into common DICOM data types. However, five of these VR types are worth noting. LT (long text), which can be 10 KB (10240 bytes), UT (unlimited Text) and OF (Other Floating point) which can theoretically be 2 to the power of 32 bytes, and OW (Other Word) and OB (Other Byte) which can be streams of undetermined sizes of 16 or 8-bit data, respectively. For analytics purposes, these big data types are usually representing image data or contain actual values far less than the maximum permissible size, which makes them not required in the former and convertible to usable type in the latter case.

In some embodiments, DWMM 118 may include functionality for obtaining and storing some medical imaging data (e.g., DICOM data or imaging metadata) while filtering or not storing other medical imaging data. For example, a single data image, based on resolution and compression, may be from a couple of hundred kilobytes to a couple of thousand kilobytes, but modalities such as Spiral CT Scans, MRIs, fMRI, etc. can have thousands of images and easily reach sizes in the order of 3-5 gigabytes. From the analytics standpoint, the storing of image data itself is not practical because it turns the data warehouse into a PACS system and can easily overflow the resources of data warehouse system 100. Image metadata, on the other hand, is typically not more than a couple of dozen kilobytes and a large portion of it may be common among images from the same image series, therefore keeping only the metadata has the advantage of enabling analytics operations without overloading the operational capacity of data warehouse system 100.

In some embodiments, DWMM 118 may include functionality for analyzing, filtering, and/or improving medical imaging data, particular human- or operator-supplied data. For example, data coming from data sources 104-112 generally has two main origins. Some of the data (e.g., DICOM tags and values) may be supplied by imaging device(s) 104, such as tube voltage and table speed, and are generally accurate as long as the device is in commission. Others, such as a patient name or a patient ID, may be supplied by a device operator or queried by RIS 106 from EMR system 108 and are subject to the same data quality issues as other human-supplied information. In this example, DWMM 118 may include an algorithm or other mechanisms for determining the quality of data received from data sources 104-112 and, depending on the determination, DWMM 118 may notify an operator (e.g., for validation of suspect data), discard the suspect data, or attempt to independently validate the suspect data, e.g., using a different data source or data repository.

Data warehouse 120 may represent any suitable entity or entities (e.g., a memory or data storage system) for storing various data from one or more data sources. For example, data warehouse 120 may be implemented using memory 116 and/or other memories across one or more computing platforms. In this example, data warehouse 120 may be accessible by DWMM 118, DWM server 102, and/or other entities (e.g., client machines).

In some embodiments, data warehouse 120 may be implemented using one or more data models for organizing data (e.g., from one or more of data sources 104-112) into data objects and/or for establishing relationships between the data objects. For example, a logical data model may be independent of a data management technology and may include data objects and information for organizing different data into the data objects. In this example, each data object may represent one or more data structures for storing data about a particular entity (e.g., a patient, a device, a hospital, an intervention, an observation, etc.). In some embodiments, a logical data model may include object oriented classes, descriptions of tables (e.g., columns, keys, triggers, etc.), and/or XML tags for storing data or implementing data objects.

In some embodiments, DWMM 118 may include functionality for utilizing one or more data models so as to organize and make accessible medical related data from various data sources 104-112. For example, using a data model, DWMM 118 may store EHR data about a patient, including a person's age, name, social security number, and other medical information, such as blood pressure and family medical history in a patient data object (e.g., one or more database tables) in data warehouse 120. Continuing with this example, EHR data about family members of the patient may each be stored in a separate patient data object and identifiers and/or other mechanisms may be used to link these patient data objects together. Similarly, other data from other data sources 104-112 may be stored in these patient data objects or in various other data objects. By storing and organizing data from various data sources 104-112 into accessible data objects, a data warehouse operator (e.g., a physician or hospital administrator) may analyze disparate and/or heterogeneous healthcare related information.

In some embodiments, a data model associated with data warehouse 120 may be modified or extended for storing medical imaging data (e.g., DICOM metadata and images). For example, a data model associated with data warehouse 120 may be modified or extended to include imaging related data objects for storing and/or organizing medical imaging data, e.g., from imaging devices 104. In this example, using an extended data model, medical imaging data may be stored in data warehouse 120 and may be leveraged for various purposes, including business analytics, quality assurance, and patient care. Additional details regarding data models and data objects for storing medical imaging data is disclosed below with regards to FIGS. 2-5.

In some embodiments, DWMM 118 may leverage data warehouse, including medical imaging data, for managing patient care and/or for influencing patient protocols and/or evaluations. For example, at an oncology center that is evaluating the value of ordering an early bone scan for every patient with low stage prostate cancer, a data warehouse operator may utilize data warehouse 120 and/or imaging related data objects therein, along with a concern data object (e.g., a data object that stored procedure outcome and/or patient outcome information), for selecting relevant patients that had early bone scans with low stage prostate cancer. In this example, the data warehouse operator may utilize data warehouse 120 for cross referencing the patients to outcomes, costs, duration of stay, number of visits, etc. stored in the concern data object and may further compare the patients to patients who had the same stage of prostate cancer but did not have a bone scan as their initial study.

In some embodiments, DWMM 118 may leverage data warehouse 120, including medical imaging data, for managing adherence to evidence-based guidelines and/or quality assurance. For example, a number of imaging related data objects may be associated with imaging device settings and quality of images from the imaging device with these settings.

In some embodiments, DWMM 118 may leverage data warehouse 120, including medical imaging data, for evaluating and monitoring workload on imaging device(s) 104. For example, using workload information and other data stored in imaging related data objects, a data warehouse operator may optimize calibration, quality control, spare part ordering, and storage of imaging device(s) 104. In another example, using workload information and other data, a data warehouse operator may allocate and schedule imaging device(s) 104 more efficiently, e.g., so that equipment depreciation and maintenance costs are minimized.

In some embodiments, DWMM 118 may leverage data warehouse 120, including medical imaging data, for facilitating management and administration of imaging departments and/or service lines. For example, DWMM 118 may provide a user interface for administrators to view and administer different aspects of imaging activities, such as personnel allocation, resource allocation, usage, and scheduling. In this example, the administrator may utilize data warehouse 120 and/or imaging related data objects therein for analyzing a procedure time for a specific imaging activity based on a technician and/or may identify areas where training or guidance are needed. In another example, the administrator may utilize data warehouse 120 and/or imaging related data objects therein for analyzing imaging quality and determining whether imaging devices are being configured correctly so as to avoid incomplete/missing information on the patient and/or avoid repeating procedures.

Table 1 below depicts various goals and related business intelligence (BI) analyses that can be leverage using data, including medical imaging data, from data sources 104-112. In particular, a data warehouse operator (e.g., a user of data warehouse system 100) may utilize data warehouse 120 to analyze data from various data sources 104-112 (e.g., healthcare related enterprise systems) and may use the data analysis for ensuring patient safety, ensuring follow-up procedures are performed, avoiding unnecessary interventions (e.g., tests and/or procedures), improving accuracy of interpretation (e.g., of test results), improving patient satisfaction, improving patient health, and improving detection (e.g., diagnosis) accuracy.

TABLE 1

| Goal | Example | Business Intelligence Analysis |
| --- | --- | --- |
| Ensure patient safety | Keep patient exposure to radiation as low as possible | How many patients have had CT scans both with and without contrast? Was it indicated? |
| Follow up | Make sure a positive screening test, such as mammogram, is properly followed | How many patients have had follow-up after a positive screening mamography? How many have had a diagnostic mamography without a screening mammography - positive or negative? |
| Avoid unnecessary Interventions (Tests and/or Procedures) | Reduce risk, stress and cost due to unnecessary tests and procedures | How many patients have had an MRI for low back pain before any other intervention such as physical therapy for six weeks? Was there a reason for early MRI? |
| Improve Accuracy of Interpretation | Reduce risk of repeat procedures and cost of delayed treatment | What have been the rate, concurrence, severity and impact of the errors in interpretation by specialist, facility, and modality? |
| Improve patient satisfaction | Reduce turnaround time | What is the time between completion of examination and the time of final report? What is the track record/performance of a specific facility or department as it relates to patient satisfaction? |
| Improve patient health | Increase communication among service providers | How often unexpected results were communicated to the appropriate physician and documented in the final report? |
| Improve Accuracy of detection | Increase quality of technical process steps | How much of the small or large intestine was adequately filled with oral contrast material? |

In some embodiments, DWMM 118 may store information about actors (e.g., physicians and/or technicians) using one or more actor data objects. Each actor data object may include data elements (e.g., attributes) and/or may define or indicate relationships between one or more other data objects. For example, a service provider data object may include information about a medical physicist, a clinician, an executive, an imaging service line manager, a researcher, or other healthcare worker. In this example, the service provider data object may include personal and professional information about the actor and may include identifiers associated with various other data objects, e.g., a patient data object or an intervention (e.g., a procedure or service rendered).

Table 2 below depicts various actors associated with example use cases related to their specific roles. In particular, a data warehouse operator (e.g., a user of data warehouse system 100) may utilize one or more actor data objects, along with medical imaging data and/or other information, to perform various data analysis associated with a given actor or example use case.

TABLE 2

| Actor | Example Use Cases |
| --- | --- |
| Medical Physicist | How are imaging devices performing? Which ones are not? By Time period, intervention type, frequency of usage, scheduling. Tracking and managing device and/or device component lifecycles and obsolescence/device type, frequency of usage, intervention type, and time period. |
| Clinician | Measuring adherence to clinical guidelines/service provider (SP), SP Type, Department, diagnosis, anatomical site, patient demographics, and modality. Measuring and managing patient compliance and adherence to treatment plans/diagnosis, patient demographics, age band, location. Integrate with Molecular Medicine analytics to determine which biomarkers and/or genomic characteristics are associated with Imaging findings. |
| Executive | Resource (human or device) productivity and/or performance analysis/Geography, Org Service Provider, Service Line, time range, etc. Costing, Profitability, and Revenue analysis by various dimensions such as the above |
| Imaging Service Line Manager | Analyzes operational performance including availability, scheduling, and utilization Resource (human or device) productivity and/or performance analytics Reimbursement and/or revenue cycle analytics as it relates to imaging at the service line level |
| Researcher | Cohort identification and/or analysis/patient demographics, imaging intervention, diagnosis Analyze correlations between modalities, device type, usage, and outcomes |

Additional details regarding a healthcare related data warehouse can be found in "Oracle® Healthcare Data Warehouse Foundation Secure Installation and Configuration Guide", Release 6.0", June 2014, http://docs.oracle.com/cd/E27737_03/doc.60/e27595.pdf; the disclosure of which is incorporated herein by reference in its entirety.

It will be appreciated that FIG. 1 is for illustrative purposes and that various nodes, their locations, and/or their functions described above in relation to FIG. 1 may be changed, altered, added, or removed. For example, some nodes and/or functions may be combined into a single entity, e.g., DWMM 118 may be integrated with DWM server 102 or another entity.

Figure 2:
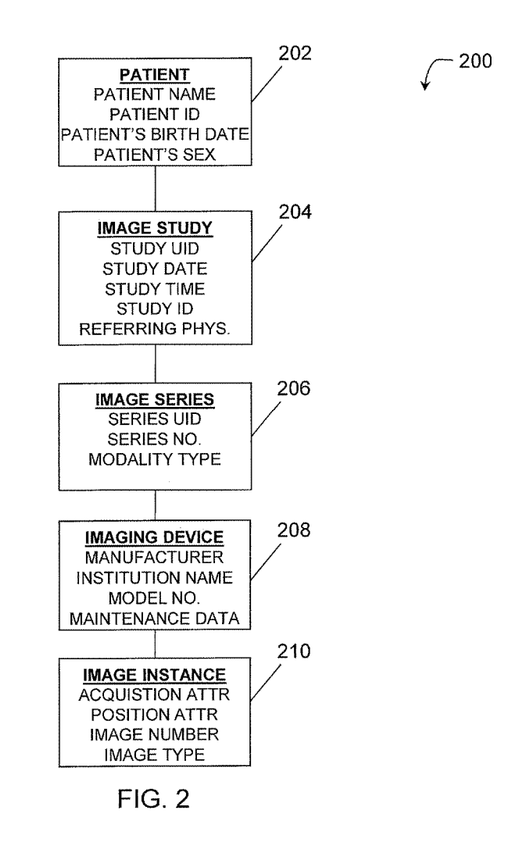
FIG. 2 is a diagram illustrating imaging related data objects according to an embodiment of the subject matter described herein.

FIG. 2 is a diagram illustrating imaging related data objects 200 according to an embodiment of the subject matter described herein. Each of imaging related data objects 200 may include or represent data elements (e.g., attributes) associated with medical imaging data, medical imaging interventions, and/or imaging device(s) 104. Each of imaging related data objects 200 may also include or represent relationships (e.g., a many to one or one to many relationship) between one or more other data objects. For example, imaging related data objects 200 may include a patient data object 202, an image study data object 204, an image series data object 206, an imaging device data object 208, and an image instance data object 210.

Patient data object 202 may represent a logical entity and/or data structure for storing information associated with a patient. For example, patient data object 202 may store information about a patient undergoing a CT scan or a sonogram. In this example, patient data object 202 may include multiple attributes, such as a patient's name, a patient identifier, a patient's birth date, a patient's sex, and/or other information.

Image study data object 204 may represent a logical entity and/or data structure for storing information associated with images from a particular intervention or study (e.g., a procedure or wellness visit). For example, image study data object 204 may store information about a set of images associated a doctor's visit on a particular date. In this example, image study data object 204 may include multiple attributes, such as an image study universal identifier (UID), a study date, a study time, a study identifier, a referring physician, and/or other information.

Image series data object 206 may represent a logical entity and/or data structure for storing information associated with a group or series of images. For example, image series data object 206 may store information about a set of images associated with X-rays of a right arm or a CT scan of a human brain. In this example, image series data object 206 may include multiple attributes, such as an image series UID, a series number, a modality type (e.g., imaging technology used), and/or other information.

Imaging device data object 208 may represent a logical entity and/or data structure for storing information associated with imaging device. For example, imaging device data object 208 may store hardware information associated with one or more imaging devices, such as a CT scanner or an X-ray machine. In this example, imaging device data object 208 may include multiple attributes, such as an image device identifier, a manufacturer, an institution name (e.g., a hospital name or location), a model number, maintenance data, related image instance identifiers, and/or other information.

Image instance data object 210 may represent a logical entity and/or data structure for storing information associated with an image instance. For example, image instance data object 210 may store information associated with one or more images, such as a CT image or an X-ray. In this example, image instance data object 210 may include multiple attributes, such as acquisition attributes, position attributes, an image number, an image type, one or more image pixel attributes, and/or other information.

In some embodiments, medical imaging data stored in imaging related data objects 200 may include DICOM data from a DICOM data source (e.g., a DICOM compliant file or message). DICOM is an object-oriented image management and messaging standard developed since 1982 by the joint effort of the American College of Radiology (ACR) and the National Electrical Manufactures Association (NEMA) for ensuring that medical systems are compatible in acquiring, storing, sending, receiving, printing, and processing medical images, as well as for creating an interoperable way of querying and retrieving those images and related documents.

In some embodiments, DICOM data sources may include medical imaging data and/or imaging metadata organized based on a DICOM image information object definition (IOD) or a DICOM data model. The DICOM data model or IOD may define IEs, e.g., patient, image study, image series, an image instance, and/or other (e.g., optional or vendor specific) IEs. Each IE may include modules and each module may include one or more attributes (e.g., data elements). Some attributes may include multiple attributes or data types.

In some embodiments, DICOM IEs (e.g., a DICOM image study IE and a DICOM image series IE) may be mapped to respective data objects, e.g., an image study data object 204 and an image series data object 206.

It will also be appreciated that imaging related data objects 200 are for illustrative purposes. Further, it will appreciated that additional and/or different data objects and/or attributes than those depicted in FIG. 2 may be usable for storing healthcare related data. Furthermore, each data object may have various relationships (e.g., many to one, one to many, etc.) and/or dependencies with regard to other data objects.

Figure 3:
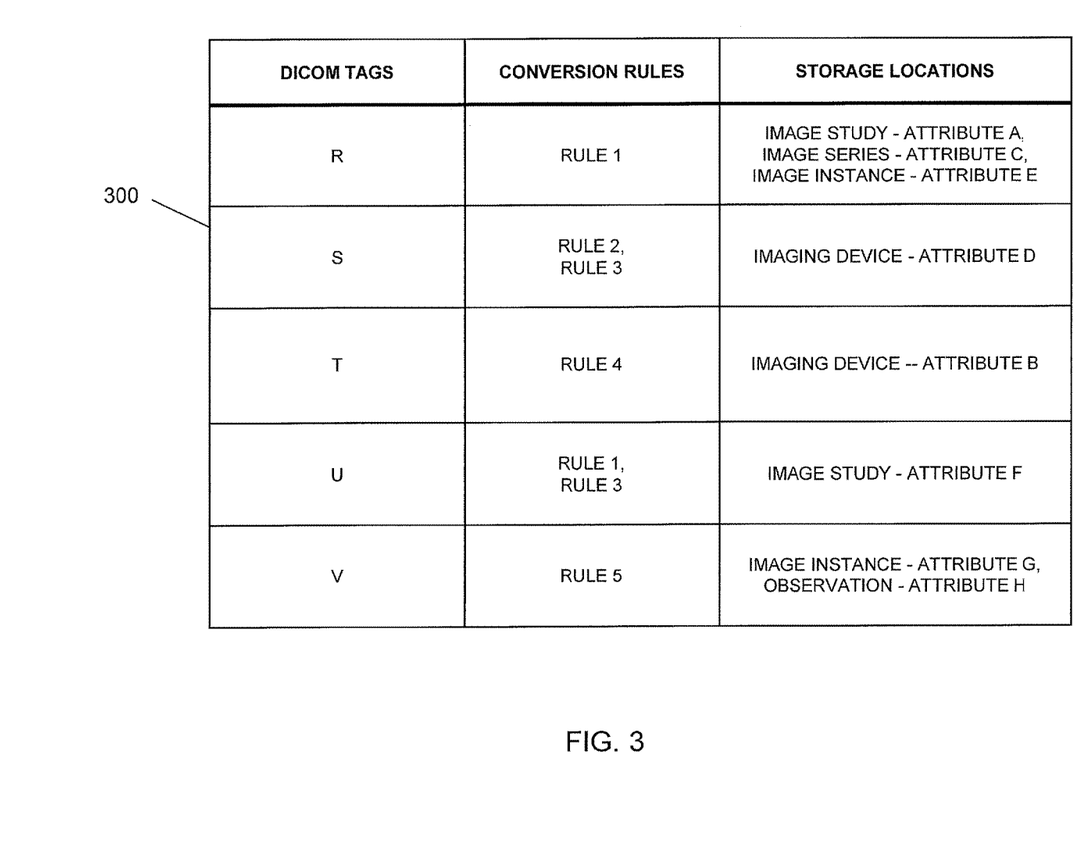
FIG. 3 is a diagram illustrating data for storing medical imaging data according to an embodiment of the subject matter described herein.

FIG. 3 is a diagram illustrating data 300 for storing medical imaging data according to an embodiment of the subject matter described herein. Data 300 may include DICOM tags, conversion rules for identifying or converting DICOM data, and storage locations for storing medical imaging data. In some embodiments, data 300 may be accessed by data warehouse system 100, DWM server 102, DWMM 118, and/or another entity and may be stored using various data structures (e.g., in memory 116).

In some embodiments, data 300 may be usable (e.g., by DWMM 118) to inspect a DICOM data source (e.g., a DICOM compliant file or message) and to obtain and/or convert at least some DICOM data from the DICOM data source. In such embodiments, after obtaining and/or converting the DICOM data, data 300 may determine one or more locations (e.g., as an attribute or data element of one or more data objects) for storing the DICOM data.

Referring to FIG. 3, data 300 may be usable for converting and/or identifying DICOM data and storing the information into one or more imaging related data objects. In some embodiments, data 300 may include associations between DICOM tags, conversion rules, and storage locations. For example, as depicted in FIG. 3, a DICOM tag 'A' may be associated with a conversion rule '1' and a storage location, e.g., multiple data objects, including an image study data object 204, an image series data object 206, and an image instance data object 210. In another example, a DICOM tag 'B' may be associated with conversion rules '2' and '3' and an attribute associated with an image instance data object 210.

Each DICOM tag in data 300 may represent a DICOM compliant tag and/or one or more related data elements (e.g., attributes or values). For example, a DICOM compliant file may be associated with a CT scanner device. In this example, the DICOM compliant file may include public tags (e.g., standardized or well-defined tags) and/or private tags (e.g., custom or proprietary tags) associated with the CT scanner device or images generated by the device. In this example, one or more DICOM tags may include data elements that include one or more data types. For example, a data element may be nested and include values, dates, and/or strings of characters.

Each conversion rule in data 300 may represent one or more information (e.g., computer executable instructions) for converting or otherwise obtaining relevant information associated with a DICOM tag from a DICOM data source. For example, a conversion rule may be usable (e.g., by DWMM 118) to convert some information from a DICOM data element from one format into another format. In another example, where a DICOM data element has multiple nested data elements or values, a conversion rule may be usable (e.g., by DWMM 118) to retrieve some information from one of the nested data elements or values.

In some embodiments, a DICOM tag may be associated with multiple conversion rules. For example, a DICOM tag may require processing before obtained data is in a compatible format for storing in data warehouse 120. In some embodiments, a conversion rule may be associated with different DICOM tags. For example, a conversion rule for converting a date value from a European format (e.g., YYYY/MM/DD) to a United States format (e.g., DD/MM/YYYY) may be used for converting any dates stored in a DICOM compliant file in data warehouse 120.

Each storage location in data 300 may represent one or more locations (e.g., data objects or attributes therein) for storing data associated with a DICOM tag. For example, a storage location may indicate an image instance data object 210 or one or more attributes therein. In this example, after DICOM data has been identified and/or converted using data 300, DWMM 118 may store the data in data warehouse 120 based on the associated storage location.

Figure 4:
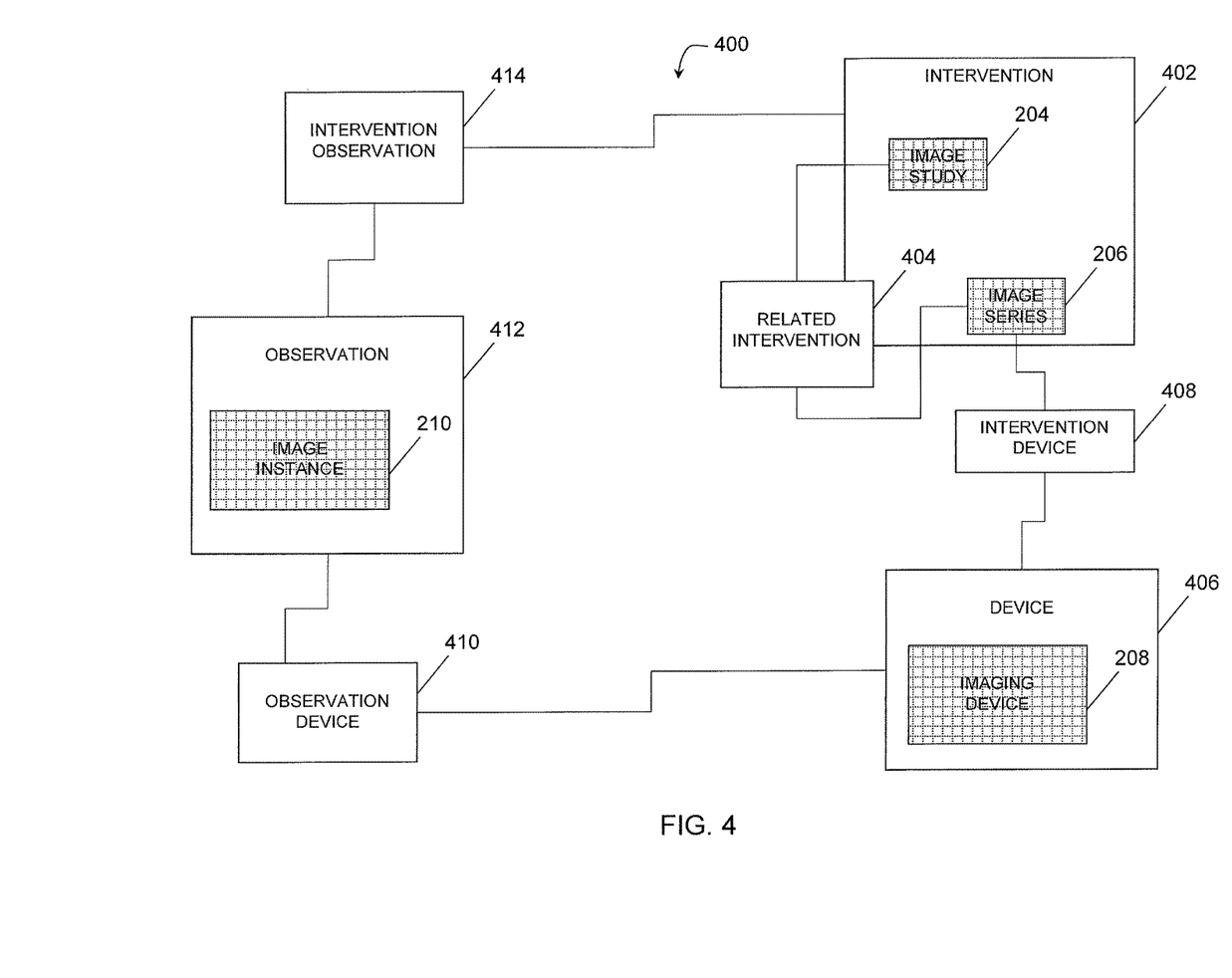
FIG. 4 is a diagram illustrating a logical data model associated with a data warehouse system according to an embodiment of the subject matter described herein.

In some embodiments, a DICOM tag may be associated with multiple storage location and vice versa. For example, a DICOM tag may include some data that may be stored in image instance data object 210 and observation data object 412.

In some embodiments, data 300 may be usable for mapping DICOM data to data objects associated with data warehouse 120. For example, a DICOM IOD or data therein may be mapped to one or more data objects. For example, patient data from a DICOM compliant file may be mapped to a patient data object 202, visit data from a DICOM compliant file may be mapped to an encounter data object, clinical trial data from a DICOM compliant file may be mapped to an image study data object 204, and trial subject data from a DICOM compliant file may be mapped to a human subject data object.

It will also be appreciated that data 300 is for illustrative purposes and that different and/or additional data than the data depicted in FIG. 3 may be usable for storing healthcare related data, including medical imaging data.

FIG. 4 is a diagram illustrating a logical data model 400 associated with data warehouse system 100 according to an embodiment of the subject matter described herein. Referring to FIG. 4, logical data model 400 may represent multiple data objects (e.g., data structures) that include information from various data sources. Data objects may represent a logical entity and may include any data structure or data construct for storing fields, attributes, data elements, or information associated with the represented entity. For example, logical data model 400 may include data objects for storing information about people (e.g., actors), medical devices (e.g., imaging device(s) 104), events (e.g., an image study, an intervention, and an observation), and/or other things (e.g., an image instance).

In some embodiments, logical data model 400 may include data objects for storing healthcare related information. Exemplary medical related data objects may include an intervention data object 402, a related intervention data object 404, a device data object 406, an intervention device data object 408, an observation device data object 410, an observation data object 412, and/or an intervention observation data object 414.

In some embodiments, logical data model 400 may be modified to include or integrate one or more imaging related data objects 200. For example, logical data model 400 may include an image study data object 204, an image series data object 206, an imaging device data object 208, and/or an image instance data object 210.

In some embodiments, one or more imaging related data objects 200 may be associated with (e.g., a subtype of) another data object and may include at least some attributes or data elements associated with the other data object. For example, image instance data object 210 may inherit or include at least some attributes, fields, or data elements from observation data object 412.

Intervention data object 402 may represent a logical entity (e.g., a data structure) for storing information associated with an intervention (e.g., a diagnostic test or procedure). For example, intervention data object 402 may store information associated with one or more medical procedures. In this example, intervention data object 402 may include multiple attributes, such as an intervention identifier, a referring physician identifier, and a results or intervention observation identifier.

In some embodiments, intervention data object 402 may be associated with a study data object 204 and an image series data object 206. For example, intervention data object 402 may include multiple identifiers associated with image study data object 204 and image series data object 206. In this example, these identifiers may be usable for accessing or querying these related data objects such that additional information regarding an image study or image series related to a given interaction can be obtained.

Related intervention data object 404 may represent a logical entity and/or data structure for storing information for associating intervention data objects 402 and/or related data objects. For example, related intervention data object 404 may store information associating image study data object 204 and image series data object 206. In this example, related intervention data object 404 may include information indicating reasons for associations and/or identifiers of the related data objects.

Device data object 406 may represent a logical entity and/or data structure for storing information associated with a medical device. For example, device data object 406 may store information associated with one or more medical devices. In this example, device data object 406 may include multiple attributes, such as a device identifier, a model number, and usage settings.

Intervention device data object 408 may represent a logical entity and/or data structure for storing information associated with a device used in or during an intervention. For example, intervention device data object 408 may store information associated with one or more medical devices. In this example, intervention device data object 408 may include multiple attributes, such as an intervention device identifier, a model number, usage settings, and a related intervention identifier.

In some embodiments, an intervention device data object 408 may represent a subtype data object (e.g., a child data object) of device data object 406. In such embodiments, intervention device data object 408 may include at least some attributes of device data object 406 and additional attributes.

Imaging device data object 208 may represent a logical entity and/or data structure for storing information associated with an imaging device. For example, imaging device data object 208 may store hardware information associated with one or more imaging devices, such as a CT scanner or an X-ray machine. In this example, imaging device data object 208 may include multiple attributes, such as an image device identifier, a model number, usage settings, and a related image instance identifiers.

In some embodiments, imaging device data object 208 may represent a subtype data object (e.g., a child data object) of one or more other data objects (e.g., parent data objects), such as device data object 406 and/or intervention device data object 408. In this example, imaging device data object 208 may include at least some attributes of other data objects and additional attributes.

Observation device data object 410 may represent a logical entity and/or data structure for storing information associated with a device used in or during an observation (e.g., when diagnosing or analyzing results from an intervention). For example, observation device data object 410 may store information associated with one or more image display devices, e.g., a computer or a display system. In this example, observation device data object 410 may include multiple attributes, such as an observation device identifier, a model number, usage settings, a related intervention identifier, and a related observation identifier.

In some embodiments, observation device data object 410 may represent a subtype data object of one or more other data objects, such as device data object 406 and/or observation data object 412. In this example, observation device data object 410 may include at least some attributes of the other data objects and additional attributes.

Observation data object 412 may represent a logical entity and/or data structure for storing information associated with an observation (e.g., test results from an intervention). For example, observation data object 412 may store information (e.g., test results and/or images) associated with one or more observations. In this example, observation data object 412 may include multiple attributes, such as an observation identifier, a diagnosis or observation value, and a related observation device identifier.

Image instance data object 210 may represent a logical entity and/or data structure for storing information associated with an image instance. For example, image instance data object 210 may store information associated with one or more images, such as a CT image or an X-ray. In this example, image instance data object 210 may include multiple attributes, such as acquisition attributes, position attributes, an image number, an image type, and/or one or more image pixel attributes, a related observation device identifier, an image identifier, image dimensions and/or resolution, a time stamp, a related image series identifier, and a related image study identifier.

In some embodiments, image instance data object 210 may represent a subtype data object of one or more other data objects, such as observation data object 412. In this example, image instance data object 210 may include at least some attributes of the other data objects and additional attributes.

Intervention observation data object 414 may represent a logical entity and/or data structure for storing information associated with an observation and a related intervention. For example, intervention observation data object 414 may store observation information (e.g., test results and/or images) associated with one or more interventions. In this example, intervention observation data object 414 may include multiple attributes, such as an intervention observation identifier, a related intervention identifier, and a related observation identifier.

It will also be appreciated that logical data model 400 is for illustrative purposes and that different and/or additional data objects than those depicted in FIG. 4 may be usable for storing healthcare related data, including medical imaging data.

Figure 5:
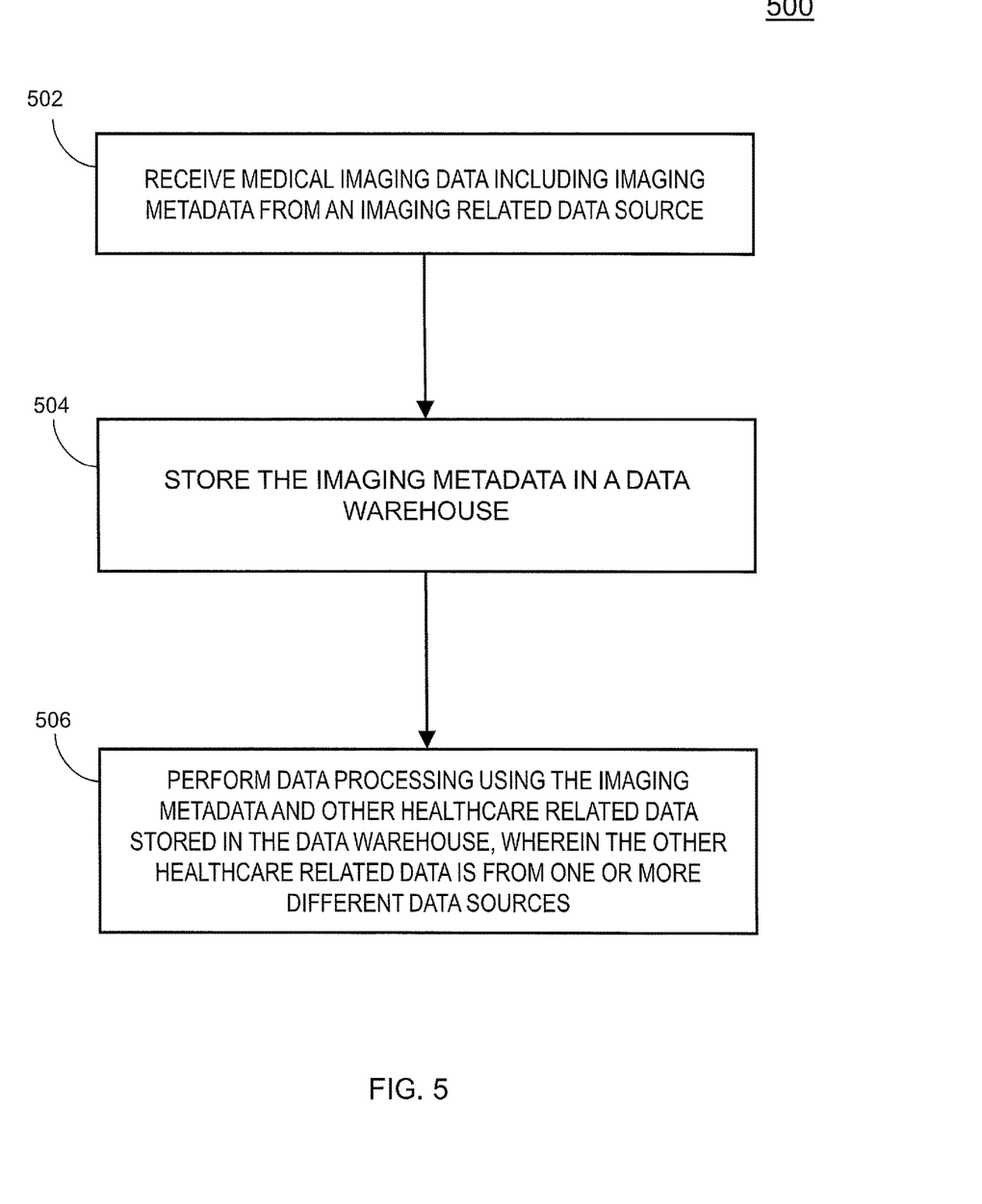
FIG. 5 is a flow chart illustrating a process for integrating medical imaging data in a data warehouse according to an embodiment of the subject matter described herein.

FIG. 5 is a flow chart illustrating a process 500 for integrating medical imaging data in a data warehouse according to an embodiment of the subject matter described herein. In some embodiments, process 500, or portions thereof, may be performed by or at data warehouse system 100, DWM server 102, DWMM 118, and/or another node, module, or entity. In some embodiments, process 500 may include steps 502, 504, and/or 506.

Process 500 may start with step 502. In step 502, medical imaging data may be received. For example, medical imaging data associated with imaging device(s) 104 may be received at DWM server 102.

In some embodiments, medical imaging data may include DICOM data. For example, medical imaging data may be received by DWM server 102 via a DICOM compliant file or a related DICOMDIR protocol.

In some embodiments, DICOM data may include information about an image, information about an imaging device, information about an image series, information about an image study, or information about a patient.

In step 504, at least a portion of the medical imaging data may be stored in a data warehouse. For example, medical imaging data may be stored in image instance data object 210 in data warehouse 120.

In some embodiments, storing at least a portion of medical imaging data in data warehouse 120 may include identifying a DICOM tag among the DICOM data and storing information associated with the DICOM tag in the at least one imaging related data object.

In some embodiments, storing at least a portion of medical imaging data in data warehouse 120 may include converting a vendor specific data portion into a different format. For example, a CT scanner may use a proprietary or custom DICOM tag for storing maintenance information or a device model number. In this example, the DICOM data from the CT scanner may be provided to DWMM 118 and may be converted into a different format or data type.

In step 506, data processing may be performed using at least the portion of the medical imaging data and other healthcare related data in the data warehouse. For example, medical imaging data may include DICOM data and other healthcare related data may include administrative information from ERP system 110 and/or patient and/or clinical information from EHR system 108.

In some embodiments, performing data processing using at least the portion of the medical imaging data and other healthcare related data in a data warehouse may include performing analytics processing, business intelligence processing, data warehouse related processing, report generation, a quality assurance analysis, a cost analysis, a load analysis, an imaging device calibration, a quality control analysis, maintenance related monitoring, resource planning, personnel scheduling, or a financial analysis.

In some embodiments, at least one imaging related data object may include a patient data object 202, an image instance data object 210, an image study data object 204, an image series data object 206, or an imaging device data object 208.

In some embodiments, at least one imaging related data object is a subtype of a non-imaging related data object. For example, image instance data object 210 may be a subtype of observation data object 412, image study data object 204 may be a subtype of intervention data object 402, an image series data object 206 may be a subtype of intervention data object 402, or imaging device data object 208 may be a subtype of device data object 406.

In some embodiments, at least one other data object in data warehouse 120 may include information from an EHR system, an HIS, an ERP system, a medical scheduling system, or a medical financial system.

It will also be appreciated that process 500 is for illustrative purposes and that different and/or additional actions may be used. It will also be appreciated that various actions described herein may occur in a different order or sequence.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for integrating medical imaging data in a data warehouse, the method comprising:
in a data warehouse management server that manages a data warehouse, the data warehouse management server including at least one processor:
receiving medical imaging data including imaging metadata from an imaging related data source;
storing, using data conversion rules, the imaging metadata in the data warehouse, wherein storing the imaging metadata includes generating image instance data objects comprising image attributes for image instances and an imaging device data object comprises attributes for an imaging device, wherein each image instance data object includes a time stamp and at least one image quality attribute, wherein the at least one imaging device data object includes an image device identifier, maintenance data, and related image instance identifiers;
performing data processing using the imaging metadata and other healthcare related data stored in the data warehouse, wherein the other healthcare related data is from one or more different data sources, wherein performing the data processing includes analyzing imaging metadata of image instance data objects associated with the related image instance identifiers of the imaging device data object and determining, using the imaging metadata and the other healthcare related data, a workload performed by the associated imaging device;
detecting imaging quality issues associated with the associated imaging device by analyzing image quality attributes of image instance data objects associated with the workload; and
notifying, via a communications interface and based on the detected imaging quality issues, an operator for imaging device calibration, imaging device training, or imaging device maintenance.

2. The method of claim 1 wherein the imaging metadata includes digital imaging and communications in medicine (DICOM) data.

3. The method of claim 2 wherein the DICOM data includes information about an image, information about an imaging device, information about an image series, information about an image study, or information about a patient.

4. The method of claim 2 wherein storing the imaging metadata in the data warehouse includes identifying a DICOM tag among the DICOM data and storing information associated with the DICOM tag in at least one imaging related data object.

5. The method of claim 4 wherein the at least one imaging related data object includes a patient data object, an image instance data object, an image study data object, an image series data object, or an imaging device data object.

6. The method of claim 4 wherein the at least one imaging related data object is a subtype of a non-imaging related data object.

7. The method of claim 1 wherein storing the imaging metadata in the data warehouse includes converting a vendor specific metadata portion into a different format.

8. The method of claim 1 wherein performing data processing using the imaging metadata and the other healthcare related data stored in the data warehouse includes performing analytics processing, business intelligence processing, data warehouse related processing, report generation, a quality assurance analysis, a cost analysis, a load analysis, a quality control analysis, resource planning, personnel scheduling, or a financial analysis.

9. The method of claim 1 wherein the other healthcare related data includes information from an electronic heath record (EHR) system, a hospital information system (HIS), an enterprise resource planning (ERP) system, a healthcare related scheduling system, or a healthcare related financial system.

10. A system for integrating medical imaging data in a data warehouse, the system comprising
at least one processor; and
a data warehouse management server that manages a data warehouse, the data warehouse management server including the at least one processor, wherein the data warehouse management server is configured to receive medical imaging data including imaging metadata from an imaging related data source, to store, using data conversion rules, the imaging metadata in the data warehouse, wherein storing the imaging metadata includes generating image instance data objects comprising image attributes for image instances and an imaging device data object comprises attributes for an imaging device, wherein each image instance data object includes a time stamp and at least one image quality attribute, wherein the at least one imaging device data object includes an image device identifier, maintenance data, and related image instance identifiers, to perform data processing using the imaging metadata and other healthcare related data stored in the data warehouse, wherein the other healthcare related data is from one or more different data sources, wherein performing the data processing includes analyzing imaging metadata of image instance data objects associated with the related image instance identifiers of the imaging device data object and determining, using the imaging metadata and the other healthcare related data, a workload performed by the associated imaging device, detecting imaging quality issues associated with the associated imaging device by analyzing image quality attributes of image instance data objects associated with the workload, and notifying, via a communications interface and based on the detected imaging quality issues, an operator for imaging device calibration, imaging device training, or imaging device maintenance.

11. The system of claim 10 wherein the imaging metadata includes digital imaging and communications in medicine (DICOM) data.

12. The system of claim 11 wherein the DICOM data includes information about an image, information about an imaging device, information about an image series, information about an image study, or information about a patient.

13. The system of claim 11 wherein the data warehouse management server is configured to identify a DICOM tag among the DICOM data and storing information associated with the DICOM tag in at least one imaging related data object.

14. The system of claim 13 wherein the at least one imaging related data object includes a patient data object, an image instance data object, an image study data object, an image series data object, or an imaging device data object.

15. The system of claim 13 wherein the at least one imaging related data object is a subtype of a non-imaging related data object.

16. The system of claim 10 wherein the data warehouse management server is configured to convert a vendor specific metadata portion into a different format.

17. The system of claim 10 wherein the data warehouse management server is configured to perform analytics processing, business intelligence processing, data warehouse related processing, report generation, a quality assurance analysis, a cost analysis, a load analysis, a quality control analysis, resource planning, personnel scheduling, or a financial analysis.

18. The system of claim 10 wherein the at least one other data object includes information from an electronic heath record (EHR) system, a hospital information system (HIS), an enterprise resource planning (ERP) system, a healthcare related scheduling system, or a healthcare related financial system.

19. A non-transitory computer readable medium having stored thereon executable instructions that when executed by a processor of a data warehouse management server that manages a data warehouse cause the data warehouse management server to perform steps comprising:

receiving medical imaging data including imaging metadata from an imaging related data source;

storing, using data conversion rules, the imaging metadata in the data warehouse, wherein storing the imaging metadata includes generating image instance data objects comprising image attributes for image instances and an imaging device data object comprises attributes for an imaging device, wherein each image instance data object includes a time stamp and at least one image quality attribute, wherein the at least one imaging device data object includes an image device identifier, maintenance data, and related image instance identifiers;

performing data processing using the imaging metadata and other healthcare related data stored in the data warehouse, wherein the other healthcare related data is from one or more different data sources, wherein performing the data processing includes analyzing imaging metadata of image instance data objects associated with the related image instance identifiers of the imaging device data object and determining, using the imaging metadata and the other healthcare related data, a workload performed by the associated imaging device;

detecting imaging quality issues associated with the associated imaging device by analyzing image quality attributes of image instance data objects associated with the workload; and notifying, via a communications interface and based on the detected imaging quality issues, an operator for imaging device calibration, imaging device training, or imaging device maintenance.

20. The non-transitory computer readable medium of claim 19 wherein the imaging metadata includes digital imaging and communications in medicine (DICOM) data.

* * * * *

UNITED STATES PATENT AND TRADEMARK OFFICE
CERTIFICATE OF CORRECTION

PATENT NO. : 10,120,976 B2
APPLICATION NO. : 14/682066
DATED : November 6, 2018
INVENTOR(S) : Natarajan et al.

Page 1 of 1

It is certified that error appears in the above-identified patent and that said Letters Patent is hereby corrected as shown below:

In the Drawings

On sheet 2 of 5, in FIG. 2, under Reference Numeral 210, Line 2, delete "ACQUISTION" and insert -- ACQUISITION --, therefor.

On sheet 5 of 5, in FIG. 5, under Reference Numeral 506, Line 2, delete "METADATAAND" and insert -- METADATA AND --, therefor.

In the Specification

In Column 2, Lines 2-3, delete "computer" and insert -- Computer --, therefor.

In Column 9, Line 9, delete "mamography?" and insert -- mammography? --, therefor.

In Column 9, Line 11, delete "mamography" and insert -- mammography --, therefor.

In the Claims

In Column 18, Line 10, in Claim 10, delete "comprising" and insert -- comprising: --, therefor.

Signed and Sealed this
Ninth Day of March, 2021

Drew Hirshfeld
*Performing the Functions and Duties of the
Under Secretary of Commerce for Intellectual Property and
Director of the United States Patent and Trademark Office*